United States Patent
Huuskonen et al.

(10) Patent No.: US 6,612,158 B1
(45) Date of Patent: Sep. 2, 2003

(54) METHOD FOR MEASURING THE TEMPERATURE AND MOISTURE OF A WEB

(75) Inventors: Reijo Huuskonen, Tikkakoski (FI); Antti Komulainen, Keuruu (FI); Matti Kurki, Jyväskylä (FI)

(73) Assignee: Metso Paper, Inc., Helsinki (FI)

( * ) Notice: Subject to any disclaimer, the term of this patent is extended or adjusted under 35 U.S.C. 154(b) by 0 days.

(21) Appl. No.: 10/049,028

(22) PCT Filed: Aug. 9, 2000

(86) PCT No.: PCT/FI00/00673

§ 371 (c)(1), (2), (4) Date: Apr. 29, 2002

(87) PCT Pub. No.: WO01/13107

PCT Pub. Date: Feb. 22, 2001

(30) Foreign Application Priority Data

Aug. 11, 1999 (FI) .............................................. 19991704

(51) Int. Cl.[7] .............................. G01N 5/02; G01L 5/04
(52) U.S. Cl. ............................................. 73/73; 73/159
(58) Field of Search ..................................... 73/73, 159

(56) References Cited

U.S. PATENT DOCUMENTS

| 1,781,153 A | 11/1930 | Allen |
| 3,595,070 A | * 7/1971 | Smith ............................ 73/73 |
| 3,618,368 A | 11/1971 | Lesemann |
| 4,532,797 A | * 8/1985 | Yang ............................... 73/75 |
| 4,877,332 A | 10/1989 | Ravensbergen |
| 5,052,233 A | 10/1991 | Rantala |
| 5,625,962 A | 5/1997 | Fleissner |

FOREIGN PATENT DOCUMENTS

| EP | 0 367 901 A2 | 5/1990 |
| JP | 11047879 A | 2/1999 |
| WO | WO 86/04412 | 7/1986 |
| WO | WO 01/13107 | 2/2001 |

OTHER PUBLICATIONS

Search report issued in Finnish priority Application No. 19991704.

* cited by examiner

*Primary Examiner*—Daniel S. Larkin
*Assistant Examiner*—Katina Wilson
(74) *Attorney, Agent, or Firm*—Lathrop & Clark LLP

(57) ABSTRACT

A web is passed over a surface (11) which is at least partly curved in the running direction of the web, which extends across the web in the cross direction, and which is placed at a distance from the web, in which connection an air cushion is formed between the moving web and the curved surface. The temperature and moisture of the web are measured indirectly by measuring the temperature and moisture of the air cushion by several detectors (41) which are in communication with openings (40) formed in the curved surface in spaced relationship with one another in the cross direction of the web.

9 Claims, 1 Drawing Sheet

METHOD FOR MEASURING THE TEMPERATURE AND MOISTURE OF A WEB

CROSS REFERENCES TO RELATED APPLICATIONS

This application is a U.S. national stage application of International Application No. PCT/FI00/00673, filed Aug. 9, 2000, and claims priority on Finnish Application No. 19991704, filed Aug. 11, 1999, the disclosures of both of which applications are incorporated by reference herein.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The invention relates to a method for measuring the temperature and moisture of a web.

In paper machines and the like in which a continuous material web is manufactured, it is necessary to measure the temperature and moisture of the material web in different parts of the process.

In the arrangements of the prior art, the temperature and moisture of the web are generally determined by means of a measuring head traversing across the web in a cross direction. In this kind of arrangement, measurement takes place at different times across the width of the web and one traversing cycle typically takes 20–40 seconds.

Commonly assigned FI patent 80522 discloses a method and an apparatus for measuring the tension of a web. The tension of the moving web is measured by placing close to the web a measurement rib which has a curved surface in the running direction of the web and in which pressure measurement detectors have been placed in holes of the rib. An air cushion is formed between the moving web and the curved surface, the air pressure in the air cushion being proportional to the tension of the web. The tension of the web is measured indirectly by measuring the pressure of this air cushion. In the method, the pressure difference between a reference pressure and the pressure of the air cushion is measured. The pressure of the air surrounding the apparatus can be used as the reference pressure or the reference pressure can be produced by a separate device.

SUMMARY OF THE INVENTION

In the method according to the invention, the apparatus disclosed in the above-mentioned FI patent 80522 can be applied in the measurement of the temperature and moisture of the web.

The invention is based on the fact that the moisture and temperature of a web are measured indirectly from an air cushion formed between the web and a surface which is at least partly curved in the running direction of the web, at the same time at several measurement points spaced from one another in the cross direction of the web. With respect to moisture, it is relative humidity that is primarily measured in the method. The value of local moisture at the point of measurement is primarily determined by the moisture of paper. The phenomenon is based on the fact that humidity tends to be distributed uniformly in the ambient air. The fast-moving web causes a strong air vortex at the points of measurement, with the result that the relative humidity of a small air space in front of a detector changes very quickly in a manner proportional to the moisture of the web moving across the measurement point.

The method according to the invention for measuring the temperature and moisture of a web is simple, reliable and accurate, and it can be employed in any part of a paper machine, such as, for example, in connection with a press section, a dryer section, a coating device, and a calender. Measurement can be performed before said section/device and/or after said section/device and/or inside said section/device.

The temperature and moisture measurement signals from each detector are passed to a monitoring system of a paper machine, which includes a computer program for computing and monitoring moisture and temperature profiles. The moisture and temperature profiles can then be used for control of various parts of the process.

In the following, the invention will be described in detail with reference to the embodiment examples of the invention illustrated in the figures of the accompanying drawing, to which the invention is not intended to be exclusively confined.

DESCRIPTION OF THE PREFERRED EMBODIMENTS

Figure 1:
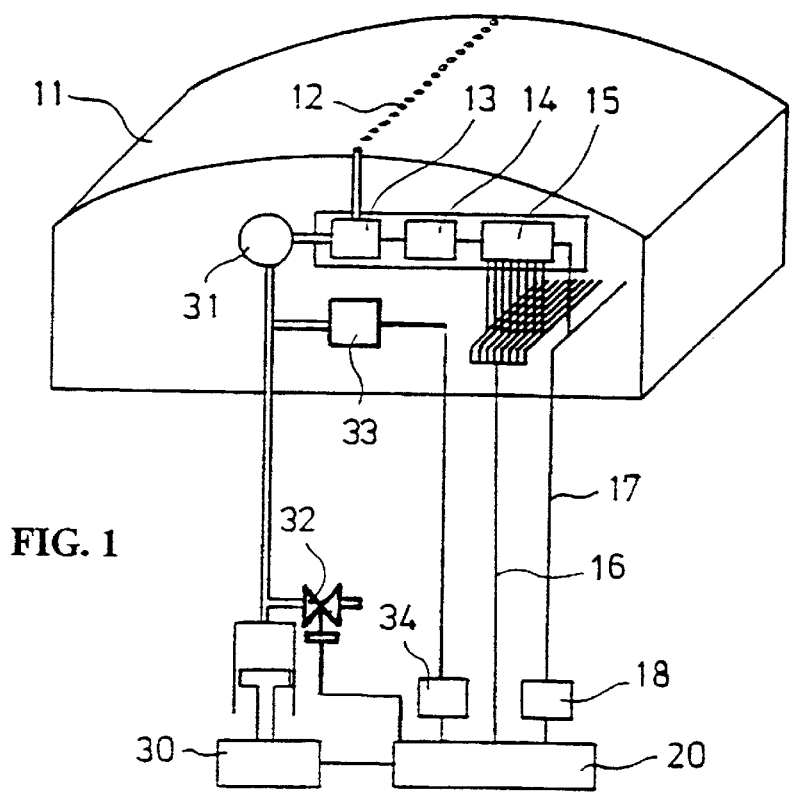
FIG. 1 is a schematic view of a known measurement system used in measuring the tension of a web, which system can be made use of in the method according to the invention.

The system shown in FIG. 1 comprises a measuring beam 11, measuring detectors 13, a control bus 16, a transmission bus 17 for measurement data, an automatic data processing apparatus 20, and a calibration system 30, 31, 32, 33. The apparatus further comprises a transducer/converters 14, 18, 34 and a multiplexer 15 needed for transmission of measurement data.

When the web runs over the measuring beam 11 extending across the entire width of the web, the air carried along with the web is pressed between the measuring beam 11 and the web, thus forming an air cushion supporting the web between the measuring beam 11 and the web. The pressure of the air cushion between the web and the measuring beam 11 corresponds in a state of balance to the roll pressure produced by the tension force of the web. The local pressure of the air cushion, and thereby the tension profile of the web, is measured by means of the sensitive differential pressure detectors 13 which are in communication with tension measurement openings 12 drilled through the top surface of the measuring beam 11.

The measuring detectors 13 are components which are based on an integrated semiconductor structure and which measure local pressure of the air cushion as compared with the known pressure of a reference pressure space 31. Pressure of the air surrounding the apparatus can be passed through a valve 32 into the reference pressure space 31 as known pressure, in which connection the ADP unit 20 controls the valve 32 so that it is opened. Reference pressure generated, for example, by means of an injector or a piston device 30 can also be passed into the reference pressure space 31 as known pressure, in which connection the ADP unit 20 controls the valve 32 so that is closed. The reference pressure can be measured by means of a precision detector 33 coupled to the reference pressure space 31, the measurement signal of which detector is passed through a converter 34 to the ADP unit 20. Each tension measurement point 12 comprises an electronics assembly 13, 14, 15 built in connection with the measuring beam 11, which assembly has been surrounded by a low rectangle in FIG. 1.

The measurement signal in the form of voltage obtained from the differential pressure detectors 13 is fed through a voltage-to-current transducer 14 to the multiplexer 15, which is controlled by the ADP unit 20 by means of the digital control bus 16. The ADP unit 20 directs a measurement signal from one differential pressure detector 13 at a time to the signal bus 17, from which it is passed through the A/D converter 18 to the ADP unit 20.

In a calibration situation, the ADP unit 20 closes the valve 32, after which the reference pressure space 31 is supplied with a reference pressure produced, for example, by means of the injector or piston device 30. At that point, the pressure of the reference pressure space 31 is also measured by means of the separate precision detector 33, the measurement signal of which is fed through the converter 34 to the ADP unit 20.

The ADP unit 20 controls the operation of the measurement system, carries out automatic calibration of the differential pressure detectors 13, reads the measurement data, processes them, and produces tension profile data in a form suitable for the operator of the system.

The pressure measuring detectors 13 associated with the tension measurement openings 12 can be located directly in the tension measurement openings 12 or there may be a passage from the tension measurement openings 12 to the detectors, in which connection the detectors can be placed more freely at a distance from the tension measurement openings 12.

Figure 2:
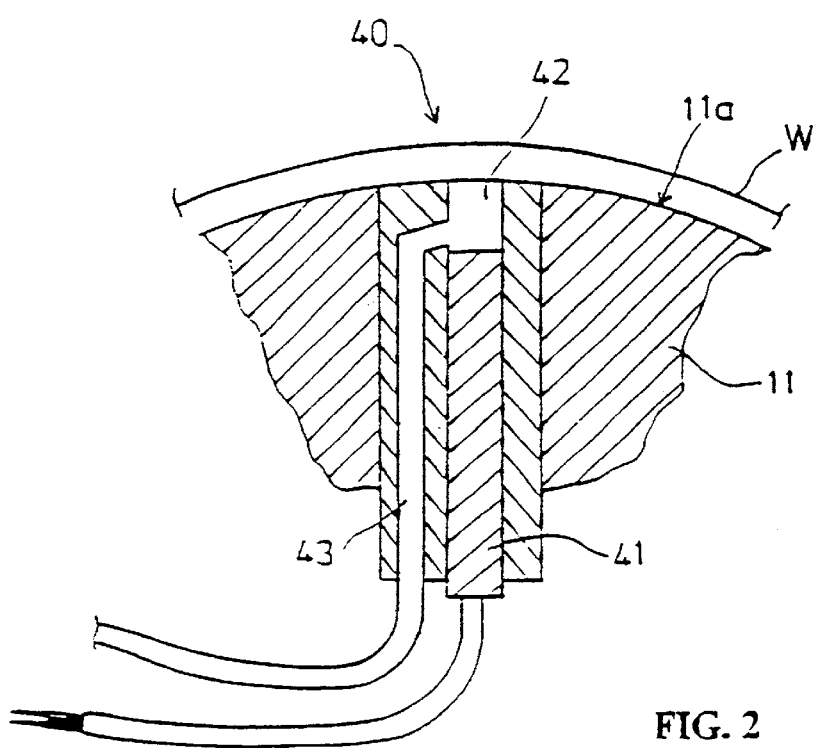
FIG. 2 is a schematic view of one measurement arrangement applying the method according to the invention.

FIG. 2 shows one measuring arrangement implementing the method according to the invention. In addition to the pressure measurement openings 12, the measuring beam 11 is provided with temperature and moisture measurement openings 40, in which an integrated detector 41 has been disposed for measuring temperature and moisture. The detector 41 is so mounted in the opening 40 that the end of the detector 41 remains at a distance from the outer surface 11a of the measuring beam 11, so that a recess 42 remains in front of the detector 41. A fast-moving web W causes a strong air vortex at the measurement points, as a result of which the relative humidity of the small air space in the recess 42 in front of the detector 41 changes very quickly proportionately with the moisture of the web W moving over the measurement point. The measurement arrangement also includes an air blowing duct 43 through which air can be blown into the recess 42 located in front of the detector 41. By blowing air from the air blowing duct 43, the recess 42 in front of the detector can be cleaned. The air blowing duct 43 can also be used for zero calibration of the moisture detector 41. In that connection, the measuring beam is moved so as to be at a distance from the web, and so-called instrument air, i.e. dry air is blown from the air blowing duct 43 into the air space 42 in front of the moisture detector 41.

The integrated detectors 41 measuring temperature and moisture can be placed in their own measurement openings 40 or they can also be placed in the same openings 12 as the pressure measuring detectors 13. It may be contemplated that the pressure measuring detectors 13 are placed in one row in the measuring beam 11 and that the temperature and moisture measuring detectors 41 are placed in another adjacent row in the measuring beam 11. It may also be contemplated that the pressure measuring detectors 13 and the temperature and moisture measuring detectors 41 are located alternately in one row in the measuring beam 11. Separate detectors may of course also be used for the measurement of temperature and moisture.

The temperature and moisture measuring detectors 41 provided in the measuring beam 11 must be insulated from the measuring beam 11 and from one another such that the temperature of the measuring beam is not able to affect the measurement result. It may also be contemplated that the detectors 41 are located beneath the curved surface of the measuring beam 11 spaced apart from one another such that air is passed to each detector 41 by means of a hose, or another similar passage from each opening 40 of the measuring beam 11. Each detector 41 shall measure only the temperature and moisture of the local air layer carried by the web W along with it and coming to the area of the detector 41 in question. The distance between the measurement points in the cross direction of the web may be, for example, in the range of about 20–200 mm.

The thickness of the air layer between the curved surface and the web is about 0.02–0.7 mm, and in the air layer there prevails a substantially laminar air flow in the running direction of the web, in which flow there occurs hardly any cross direction air flow.

Instead of the measuring beam used in the measurement of web tension, it is also possible to use a roll in which temperature and moisture measuring detectors are mounted. In that connection, the roll is stopped for the time of measurement.

The claims are presented in the following and the various details of the invention may vary within the inventive idea defined by said claims and differ, from the disclosure given above by way of example only.

What is claimed is:

1. A method for measuring the temperature and moisture of a web comprising the steps of:

positioning a measuring beam having a surface beneath the web, the surface being at least partly curved in the running direction of the web and extending across the web in the cross direction and spaced a distance from the web, an air cushion being formed between the moving web and the curved surface;

indirectly measuring the temperature and moisture of the web by measuring the temperature and moisture of said air cushion by means of a plurality of detectors which are in communication with respective first openings formed in the curved surface in spaced relationship with one another in the cross direction of the web;

positioning each detector so that a detector end is positioned at a distance from the curved surface of the beam, a recess being defined thereby between each first opening and the detector associated there with; and directing an air blow to said respective first openings in front of each detector in order to clean the recess in front of the detector.

2. The method of claim 1 further comprising the step of measuring the pressure of the air cushion between the web and the curved surface by a plurality of pressure detectors which are in communication with air pressure measurement openings in the measuring beam surface, the air pressure measurement openings being spaced from one another in the cross direction.

3. The method of claim 2 wherein each air pressure measurement opening is also in communication with one of the first openings in the curved surface.

4. An apparatus for indirectly measuring the temperature and moisture of a moving web, the apparatus comprising:

a measuring beam positioned beneath the moving web, the measuring beam having portions defining a surface curved in the running direction of the web, wherein the surface extends across the web in the cross direction and is spaced from the web, an air cushion being formed between the moving web and the curved surface;

portions of the measuring beam defining a plurality of first openings in communication with the air cushion, the first openings being spaced from one another in the cross direction;

a plurality of temperature and moisture sensors mounted to the beam to be in communication with each of the first openings, the temperature and moisture sensors providing data to an automatic data processing apparatus, wherein the temperature and the moisture of air from the air cushion in the vicinity of each first opening is measured by the temperature and moisture sensors;

each of the plurality of temperature and moisture sensors comprising an integrated temperature and moisture sensor positioned within the beam in connection with each first-opening, so that a detector end is positioned at a distance from the curved surface of the beam, a recess being defined thereby between each first opening and the integrated detector associated therewith; and an air blowing duct communicating with each recess, wherein air can be blown in to the recesses through the air blowing ducts.

5. The apparatus of claim 4 further comprising a plurality of pressure sensors positioned to communicate with each of the first openings to measure the pressure in the air cushion in the vicinity of each opening, the pressure sensors supplying data to the automatic data processing apparatus.

6. An apparatus for indirectly measuring the temperature and moisture of a moving web, the apparatus comprising:

a measuring beam positioned beneath the moving web, the measuring beam having portions defining a surface curved in the running direction of the web, wherein the surface extends across the web in the cross direction and is spaced from the web, an air cushion being formed between the moving web and the curved surface;

portions of the measuring beam defining a plurality of first openings in communication with the air cushion, the first openings being spaced from one another in the cross direction;

a plurality of temperature and moisture sensors mounted to the beam to be in communication with each of the first openings, the temperature and moisture sensors providing data to an automatic data processing apparatus, wherein air from the air cushion in the vicinity of each first opening is measured by the temperature and moisture sensors; and a plurality of pressure sensors positioned to communicate with a plurality of second openings formed in the measuring beam in communication with the air cushion, the second openings being spaced from one another in the cross direction, the pressure sensors being positioned to measure the pressure in the air cushion in the vicinity of each opening, the pressure sensors supplying data to the automatic data processing apparatus.

7. A method for measuring the temperature and moisture of a web comprising the steps of:

positioning a measuring beam having a surface beneath the web, the surface being at least partly curved in the running direction of the web and extending across the web in the cross direction and spaced a distance from the web, an air cushion being formed between the moving web and the curved surface; and indirectly measuring the temperature and moisture of the web by measuring the temperature and moisture of said air cushion by means of a plurality of detectors which are in communication with respective first openings formed in the curved surface in spaced relationship with one another in the cross diction of the web;

passing the temperature and moisture measurement signals from each detector to a monitoring system of a paper machine, which includes a computer program for computing and monitoring moisture and temperature profiles; and using said moisture and temperature profiles to control the papermaking process.

8. The method of claim 7 further comprising the step of measuring the pressure of the air cushion between the web and the curved surface by a plurality of pressure detectors which are in communication with air pressure measurement openings in the measuring beam surface, the as pressure measurement openings being spaced from one another in the cross direction.

9. The method of claim 8 wherein each air pressure measurement opening is also in communication with one of the first openings in the curved surface.

* * * * *

UNITED STATES PATENT AND TRADEMARK OFFICE
CERTIFICATE OF CORRECTION

PATENT NO. : 6,612,158 B1
DATED : September 2, 2003
INVENTOR(S) : Reijo Huuskonen et al.

It is certified that error appears in the above-identified patent and that said Letters Patent is hereby corrected as shown below:

Column 4,
Line 50, "there with" should be -- therewith --

Column 6,
Line 41, "as" should be -- air --

Signed and Sealed this

Sixteenth Day of December, 2003

JAMES E. ROGAN
*Director of the United States Patent and Trademark Office*